United States Patent [19]
Hall

[11] 3,953,598
[45] Apr. 27, 1976

[54] COMPOUNDS, COMPOSITIONS AND METHODS OF USE

[75] Inventor: Charles M. Hall, Kalamazoo, Mich.

[73] Assignee: The Upjohn Company, Kalamazoo, Mich.

[22] Filed: Sept. 23, 1974

[21] Appl. No.: 508,788

Related U.S. Application Data

[62] Division of Ser. No. 287,425, Sept. 8, 1972, Pat. No. 3,838,132.

[52] U.S. Cl. .............................................. 424/258
[51] Int. Cl.² ........................................ A61K 31/47
[58] Field of Search ................................... 424/258

[56] References Cited
UNITED STATES PATENTS

| | | | |
|---|---|---|---|
| 3,821,227 | 6/1974 | Hall et al. ............................ | 424/258 |
| 3,838,133 | 6/1974 | Hall et al. ............................ | 424/258 |
| 3,864,493 | 2/1975 | Cairns et al. ......................... | 424/283 |
| 3,879,544 | 4/1975 | Reisner et al. ....................... | 424/337 |
| 3,883,653 | 5/1975 | Barth .................................. | 424/251 |
| 3,885,038 | 5/1975 | Pfister et al. ......................... | 424/283 |

OTHER PUBLICATIONS
Chemical Abstracts, 77:75201g (1972), Waring.

Primary Examiner—Norman A. Drezin
Attorney, Agent, or Firm—Martin B. Barancik; Roman Saliwanchik

[57] ABSTRACT

Compounds of the formula

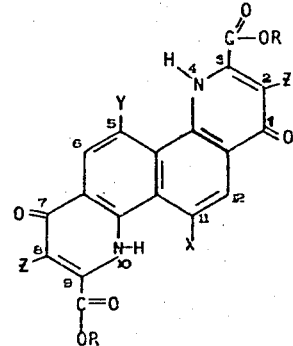

are useful in the prophylactic treatment of sensitized humans and animals for allergy and all anaphylactic reactions of a reagin or non-reagin mediated nature.

Compositions of these compounds formulated with pharmaceutical carriers and methods of using these compositions are also provided.

9 Claims, No Drawings

COMPOUNDS, COMPOSITIONS AND METHODS OF USE

This is a division of application Ser. No. 287,425, filed Sept. 8, 1972, now U.S. Pat. No. 3,838,132.

BRIEF SUMMARY OF THE INVENTION

This invention relates to novel compounds of Formula I$a$, pharmaceutical compositions employing these compounds, and a process for the prophylactic treatment of allergic conditions in sensitized mammals using these compounds.

DETAILED DESCRIPTION OF THE INVENTION

In accordance with this invention there are provided compounds represented by Structure I$a$

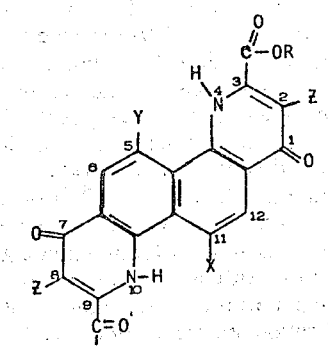

wherein it is understood that I$a$ can exist in its tautomeric form I$b$ and that the compounds of this invention are likely to be mixtures of all tautomeric forms, the percentages of each tautomer to be at least partially dependent on the nature of R, X, Y, and Z and the physical environment of the compound.

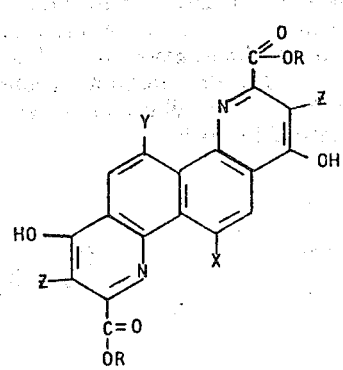

For the purpose of brevity throughout the application and appended claims, the compounds will be referred to hereinafter in their keto form, structure I$a$.

The R substituent is selected from the group consisting of hydrogen, alkyl from one to three carbon atoms, inclusive; phenyl, and a pharmaceutically acceptable metal or an amine cation.

Z is selected from the group consisting of hydrogen, alkyl from one to three carbon atoms, inclusive; and phenyl.

X and Y can be the same or different monosubstituents. When X and Y are different monosubstituents, one monosubstituent must be hydrogen and the other monosubstituent is selected from the group consisting of alkyl from one to three carbon atoms, inclusive; alkoxy from one to three carbon atoms, inclusive; phenyl; halogen; hydroxy; nitro; trifluoromethyl; cyano; amino; carboxyamide; and

where Q is selected from the group consisting of hydrogen; alkyl from one to three carbon atoms, inclusive; phenyl; and a pharmaceutically acceptable metal or amine cation, with the proviso that where R is alkyl from one to three carbon atoms, inclusive; or phenyl; then Q is an alkyl from one to three carbon atoms, inclusive; phenyl, hydrogen, or a pharmaceutically acceptable metal or amine cation, and where R is hydrogen or a pharmaceutically acceptable metal or amine cation, then Q is the same as R. When X and Y are the same monosubstituent, they are selected from the group consisting of hydrogen, chlorine, bromine, and methoxy.

The preferred compounds are those compounds where R is selected from the group consisting of hydrogen or a pharmaceutically acceptable metal or amine cation. Z is hydrogen. X and Y can be the same or different monosubstituents. When X and Y are different monosubstituents, one monosubstituent is hydrogen and the other monosubstituent is selected from the group consisting of alkyl from one to three carbon atoms, inclusive; alkoxy from one to three carbon atoms, inclusive; halogen; cyano; and

where Q is selected from the group consisting of hydrogen and a pharmaceutically acceptable metal or amine cation and is the same as R. When X and Y are the same monosubstituent, they are selected from the group consisting of hydrogen, chlorine, bromine, and methoxy.

The more preferred compounds are those compounds where R is selected from the group consisting of amine cations. Z is hydrogen. X and Y can be the same of different monosubstituents. When X and Y are different monosubstituents, one monosubstituent is hydrogen and the other monosubstituent is selected from the group consisting of alkyl from one to three carbon atoms, inclusive; alkoxy from one to three carbon atoms, inclusive; halogen; and cyano. When X and Y are the same monosubstituent, they are selected from the group consisting of hydrogen, chlorine, bromine, and methoxy.

As employed in the above disclosure and throughout the specification, the term "halogen" includes fluoro, chloro, bromo, and iodo and the term "alkyl" includes methyl, ethyl, propyl, and isopropyl when limited to three carbon atoms. The term "a pharmaceutically acceptable metal or amine cation" includes alkali metals such as sodium and potassium, alkaline earth metals such as calcium and magnesium, other acceptable metals such as aluminum, and amine cations. The term "amine cation" includes all pharmaceutically acceptable amine cations, including, for example, cations of ammonia, tris(hydroxymethyl)aminomethane, D-threo-2-amino-1-p-nitrophenyl-1,3-propanediol, N,N-bis(hydroxyethyl)piperazine, 2-amino-2-methyl-1-propanol,2-amino-2-methyl-1,3-propanediol and 2,2-bis(hydroxymethyl)-2,2',2'''-nitriolotriethanol and further amines including $H_2NR'$, $HNR'_2$, and $NR'_3$, wherein R' is selected from the group consisting of alkyl from one to three carbo atoms, inclusive, and $-CH_2CH_2OH$.

The compounds of this invention can be prepared by methods known to the art. The basic synthetic pathway employed is the reaction of an appropriately substituted naphthalene-1,5-diamine (II) with an oxaloacetate sodium salt (III) in the presence of a solvent to form the diadduct (IV). The R group is limited to an alkyl of from one to three carbon atoms, inclusive; and phenyl. Ring closure to the desired compound (Ia) is accomplished by heating the diadduct at appropriate conditions.

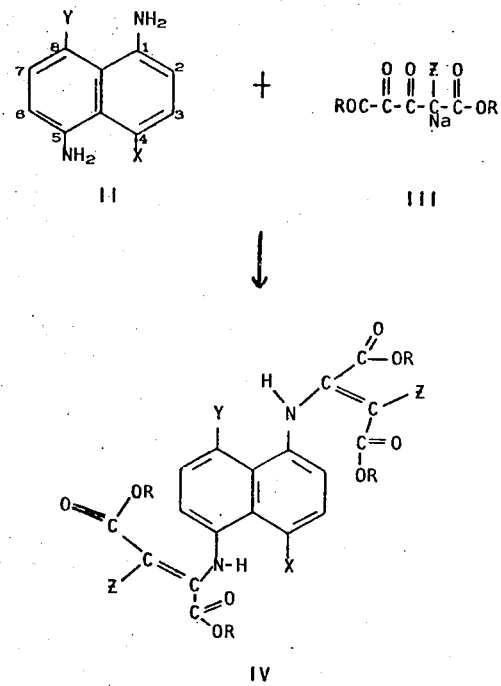

After the synthesis has been carried out, the carboxylate can be transesterified to other esters or hydrolyzed to the carboxy acid. The carboxy acid is converted to metal or amine salts by standard methods.

It should be noted that because of the symmetry of the compounds of this invention, a monosubstituent at the 5 position is equivalent to a monosubstituent at the 11 position.

The starting materials of the synthesis, X and Y substituted naphthalene-1,5-diamine compounds where X and Y are the same or different, have been prepared in the art. Examples of these compounds include naphthalene-1,5-diamine, 4,8-dibromonaphthalene-1,5-diamine, 4,8-dimethoxynaphthalene-1,5-diamine, 4-methylnaphthalene-1,5-diamine, and 4-nitronaphthalene-1,5-diamine.

X and Y substituted 1,5-dinitronaphthalene compounds where X and Y are the same or different have also been prepared in the art. Examples of these compounds include 4,8-dichloro-1,5-dinitronaphthalene, 4-chloro-1,5-dinitronaphthalene, and 4-amino-1,5-dinitronaphthalene.

Compounds with various substituents at the X and Y position and included within the scope of the invention can be conveniently prepared by going through a diazotization of the 4-amino-1,5-dinitronaphthalene starting material, placing the appropriate X substituent at the 4 position, and then reducing the dinitro compound to the diamino compound with the appropriate X or Y substituent in place, the reduction effected by treatment with hydrogen and a palladium charcoal catalyst or with iron and hydrochloric acid in ethanol.

For example, 4-amino-1,5-dinitronaphthalene is diazotized with nitrous acid formed in situ by sodium nitrite and hydrochloric acid. The diazonium salt is then contacted with potassium cyanide to form 4-cyano-1,5-dinitronaphthalene. The 4-cyano compound can be reduced to the 1,5-diamine by either of the processes disclosed above or hydrolyzed with water to 4-carboxy-1,5-dinitronaphthalene which can be esterified to any of the carboxy esters of this invention or, alternatively, the 4-carboxy-1,5-dinitronaphthalene compound is converted to 4-trifluoromethyl-1,5-dinitronaphthalene with sulfur tetrafluoride. The 4-trifluoromethyl-1,5-dinitronaphthalene can be contacted with dimethylcadmium to form the 4-acetyl-1,5-dinitro compound which is then diazotized with nitrous acid formed in situ and contacted with sodium hydroxide, thereby forming the 4-hydroxy-1,5-dinitronaphthalene compound. The 4-hydroxy is then conveniently converted to the 4-alkoxy-1,5-dinitronaphthalene compound by acylation with an appropriate alkylhalide.

The above reactions for synthesizing starting materials of this application are carried out by standard methods known to the art. Once the appropriate X or Y substituent is in place, the dinitro grouping can be reduced to the diamine by one of the disclosed methods and the compounds of the invention prepared by the synthetic pathway previously outlined.

The second reactant, the oxaloacetate derivative is also readily available. Compounds where R is ethyl and Z is hydrogen, methyl, ethyl or phenyl are known in the art.

Where Z is hydrogen, an alternative reagent to the oxaloacetate derivative is available to form the diadduct. Acetylene dicarboxylate (V), where R is limited to alkyl of from one to three carbon atoms, inclusive; or phenyl, can be added to the substituted naphthalene-1,5-diamine to form the diadduct (IV), where Z is hydrogen as illustrated below:

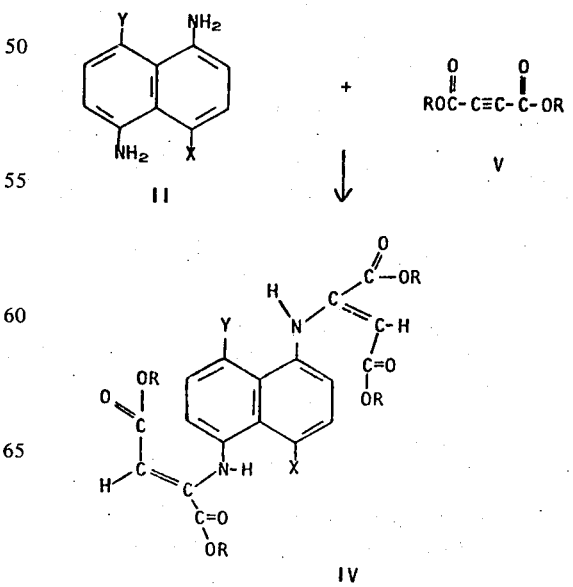

In the formation of the diadduct and subsequent ring closure, the following processing conditions can be observed.

When using the oxaloacetate reagent to form the diadduct, there should be a sufficient amount of acid present to protonate the oxaloacetate carbanion and catalyze the removal of the keto grouping. The acid can also serve as a solvent for the two reagents as well. For example, glacial acetic acid, propionic acid, p-toluene sulfonic acid, and butyric acid are acids, which can be used. If a further reagent is needed to place the two reactants into solution (or a co-solvent desired), benzene, toluene, diethylether, dioxane, tetrahydrofuran, or alcohols from one to about four carbon atoms can be employed. The length of time for the formation of the diadduct is temperature dependent. At room temperature the reaction proceeds rather slowly but as the temperature is raised, reaction time is decreased. Acceptable reaction times are achieved at temperatures ranging from about 40° to about 70°C., although reaction temperatures can be above 100°C. if desired.

With regard to the use of the acetylene dicarboxylate reactant in the formation of the diadduct, appropriate solvents are alcohols having from one to about six carbon atoms, preferably one to about three carbon atoms, benzene, diethylether, dioxane, tetrahydrofuran, or any other solvent which places both of the reactants in solution and allows the desired compound to form. Generally the reaction proceeds readily at room temperature and can be promoted by an increase in temperature to about 100°C.

Ring closure of the diadduct, prepared by the methods disclosed above, and formation of the desired compound can be accomplished by heating the diadduct at a relatively high temperature. This heating can be done to the neat diadduct. However, it is preferred to use a solvent which can function as a heat transfer medium. Any high boiling inert solvent such as a mineral oil, hexamethylphosphoric triamide, diphenyl ether, or Dowtherm A, which appears to be primarily diphenyl ether, is suitable. The ring cyclization step is preferably carried out at temperatures of from about 220°C. to about 280°C., although lower or higher temperatures can be employed if desired. Particularly preferred solvents are Dowtherm A, or diphenyl ether, which boil at about 250°C., thus enabling the ring cyclization to occur during reflux.

An additional advantage of the elevated temperature during the ring cyclization step is that any adduct formed in the preceding step which is not in a position to cyclize since it is trans to the benzene ring is isomerized to the cis configuration during the heating, thereby allowing substantial yields of the desired compound to be produced. This trans adduct preparation occurs more frequently when an aprotic solvent and acetylene dicarboxylate are used in the adduct formation step. As stated previously, at this point various esters, the acid, or salts can be prepared at the R position of the carboxy group. Different esters can be prepared by a standard transesterification reaction. Ester groups are converted to the acid by treatment with base and acid. The acid can then be easily converted to an amine salt, alkali metal, calcium, or aluminum, for example, by contacting the diacid with two equivalents of the desired amine or metal hydroxide and heating in a sufficient amount of water to effect solubilization. The crystalline salts can be precipitated by the addition of methanol. When R is hydrogen or a pharmaceutically acceptable metal or amine cation and X or Y is

then Q is the same as R.

Following is an illustrative list of starting materials and desired compounds which can be prepared by the above disclosed procedures:

TABLE II

Starting Material

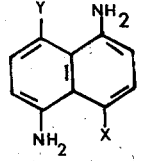

Product

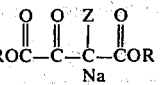

| X | Y | R |
|---|---|---|
| H | H | $CH_3$ |
| H | H | $C_2H_5$ |
| Br | H | $C_3H_7$ |
| I | H | $iC_3H_7$ |
| $CH_3$ | H | $C_6H_5$ |
| $C_2H_5$ | H | $CH_3$ |
| $C_3H_7$ | H | $C_2H_5$ |
| $iC_3H_7$ | H | $C_3H_7$ |
| $OC_2H_5$ | H | $C_6H_5$ |
| $OC_3H_7$ | H | $CH_3$ |
| $OiC_3H_7$ | H | $C_2H_5$ |
| $CF_3$ | H | $C_3H_7$ |
| $CN$ | H | $iC_3H_7$ |
| $COOH$ | H | $C_6H_5$ |
| $COOC_2H_5$ | H | $CH_3$ |

TABLE III

The above illustrative examples of Table II are prepared where Z in the oxaloacetate sodium salt is methyl, ethyl, propyl, isopropyl, or phenyl.

TABLE IV

The illustrative examples of Tables II and III are converted to compounds where R is hydrogen or a pharmaceutically acceptable metal or amine cation such as those exemplified earlier.

For reason of brevity, Tables III and IV are not rendered in the same manner as Table II, but the same illustrative scoping is intended.

The following examples are compounds in accordance with this invention. The compounds are intended not to limit but merely to exemplify the invention.

EXAMPLE 1

Dimethyl 1,4,7,10-Tetrahydro-1,7-dioxoquino-[8,7-h]quinoline-3,9-dicarboxylate a. Tetramethyl 2,2'-(1,5-naphthalenediimino)-dibutenedioate 30 Gram of dimethyl acetylenedicarboxylate was added slowly to a solution of 15.8 gram of 1,5-naphthalenediamine in 250 ml. of methanol. The mixture is stirred at room temperature for 6 hours, during which time the yellow product, a 1:2 adduct, precipitates and is collected by filtration. Recrystallization gives a yellow solid melting at 220°C.

Anal. Calcd. for: $C_{22}H_{22}N_2O_8$: C, 59.72; H, 5.01; N, 6.33. Found: C, 59.43; H, 5.00; N, 6.40. The uv, ir, and nmr spectra are in agreement with the structure.

b. Product 5.0 gram of the 1:2 adduct is added to refluxing Dowtherm A, boiling point about 250°, and the mixture is heated at the reflux temperature for 5 minutes. The reaction mixture is cooled and the yellow crystalline product collected by filtration. The melting point is greater than 310°C.

EXAMPLE 2

Disodium 1,4,7,10-tetrahydro-1,7-dioxoquino[8,7-h]quinoline-3,9-dicarboxylate 1.0 gram of the diester prepared in Example 1 is heated in 50 ml. of 1.0N NaOH for 30 minutes. The mixture is cooled, diluted with water, and methanol added. The precipitate is filtered and collected.

EXAMPLE 3

1,4,7,10-Tetrahydro-1,7-dioxoquino[8,7-h]-quinoline-3,9-dicarboxylic acid

To the cooled, diluted mixture of Example Two is added sufficient acid to adjust the pH to 3. The desired diacid precipitates and is collected by filtration. The melting point is greater than 310°C.

EXAMPLE 4

Di Tris(hydroxymethyl)methylammonium-1,4,7,10-tetrahydro-1,7-dioxoquino-[8,7-h]quinoline-3,9-dicarboxylate The diacid prepared in Example 3 is dissolved in an equivalent of aqueous tris(hydroxymethyl)-aminomethane. Methanol is added to the solution and the precipitate is collected.

The compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of Formula Ia. The preferred method of administration is by inhalation into the lung by means of an aerosol liquid or powder for insufflation. Another preferred route of administration with these compounds, particularly where R is tris(hydroxymethyl)methylammonium and Z is hydrogen, is oral.

For oral administration either solid or fluid unit dosage forms can be prepared. For preparing solid compositions such as tablets, the compound of Formula Ia is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I$a$ in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I$a$ in water or ethanol and mixing with a volatile propellant and placing in a pressurized container having a metering valve to release a predetermined amount of material.

The liquefied propellant employed is one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration. A dosage schedule of from about 0.01 to about 10 mg. of compound in a single dose administered parenterally or by inhalation in the compositions of this invention is effective for preventing allergy attacks. More specifically, the single dose is from about 0.05 to about 1 mg. of compound. The oral and rectal dose is from about 0.1 to about 20 mg. in a single dose. More specifically, the single dose is from about 0.1 to about 5 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 0.05 mg. of the tris-(hydroxymethyl)aminomethane salt of 1,4,7,10-tetrahydro-1,7-dioxoquino[8,7-h]quinoline-3,9-dicarboxylic acid. Four hours later the individual insufflates 0.0005 mg. of the same compound and every 4 to 6 hours thereafter insufflates 0.0005 mg. of the same compound until effective asthma prophylaxis is not provided. The individual then insufflates 0.05 mg. of the same compound, then reduces the insufflation dosage to 0.0005 mg. 4 to 6 hours later. The dosage schedule continues in this manner.

The administration of the compositions of the present invention to humans and animals provides a method for the prophylactic treatment of allergy or all anaphylactic reactions of a reagin or a non-reagin mediated nature. That is to say these compositions, when administered to a sensitized individual prior to the time that the individual comes into contact with substances (antigens) to which he is allergic, will prevent the allergic reaction which would otherwise occur.

EXAMPLE 5

A lot of 10,000 tablets, each containing 1 mg. of dimethyl 1,4,7,10-tetrahydro-1,7-dioxoquino[8,7-h]-quinoline-3,9-dicarboxylate is prepared from the following types and amounts of ingredients:

| | |
|---|---|
| Dimethyl 1,4,7,10-tetrahydro-<br>1,7-dioxoquino[8,7-h]quinoline-<br>3,9-carboxylate | 10 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 12 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of 1 tablet every 4 to 6 hours.

EXAMPLE 6

One thousand two-piece hard gelatin capsules, each containing 1 mg. of disodium 1,4,7,10-tetrahydro-1,7-dioxoquino[8,7-h]quinoline-3,9-carboxylate are prepared from the following types and amounts of ingredients:

| | |
|---|---|
| Disodium 1,4,7,10-tetrahydro-<br>1,7-dioxoquino[8,7-h]quinoline-<br>3,9-dicarboxylate | 1 Gm. |
| Talc | 150 Gm. |
| Magnesium stearate | 1 Gm. |

The ingredients are mixed well and filled into capsules of the proper size.

Capsules so prepared are useful in preventing attacks of bronchial asthma at a dose of one capsule every 4 to 6 hours.

EXAMPLE 7

One thousand tablets, each containing 1 mg. of dimethyl 1,4,7,10-tetrahydro-1,7-dioxoquino[8,7-h]quinoline-3,9-dicarboxylate are prepared from the following types and amounts of ingredients:

| | |
|---|---|
| Dimethyl 1,4,7,10-tetrahydro-<br>1,7-dioxoquino[8,7-h]quinoline-<br>3,9-carboxylate | 1 Gm. |
| Microcrystalline cellulose NF | 420 gm. |
| Starch | 100 Gm. |
| Magnesium stearate powder | 5 Gm. |

The ingredients are screened and blended together and pressed into 526 mg. tablets.

The tablets are useful to protect against food allergy at a dose of 1 tablet before meals.

EXAMPLE 8

A sterile preparation suitable for intramuscular injection and containing 0.1 mg. of disodium 1,4,7,10-tetrahydro-1,7-dioxoquino[8,7-h]quinoline-3,9-dicarboxylate in each milliliter is prepared from the following ingredients:

| | |
|---|---|
| Disodium 1,4,7,10-tetrahydro-<br>1,7-dioxoquino[8,7-h]quinoline-<br>3,9-dicarboxylate | 0.1 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for prophylactic treatment of allergic rhinitis.

EXAMPLE 9

Six hundred ml. of an aqueous solution containing 0.1 mg. of tris(hydroxymethyl)aminomethane salt of 1,4,7,10-tetrahydro-1,7-dioxoquino[8,7-h]quinoline-3,9-carboxylic acid per ml. is prepared as follows:

| | |
|---|---|
| Tris(hydroxymethyl)-<br>aminomethane salt of<br>1,4,7,10-tetrahydro-<br>1,7-dioxoquino[8,7-h]quino-<br>line-3,9-dicarboxylic acid | 60 mg. |
| Sodium chloride | 0.6 Gm. |
| Water for injection q.s. | 600 ml. |

The THAM salt and sodium chloride are dissolved in sufficient water to make 600 ml. and sterile filtered.

The solution is placed in nebulizers designed to deliver 0.25 ml. of solution per spray.

The solution is inhaled into the lungs every 4 to 6 hours for prevention of asthmatic attacks.

EXAMPLE 10

A powder mixture consisting of 5 mg. of tris(hydroxymethyl)aminomethane salt of 1,4,7,10-tetrahydro-1,7-dioxoquino[8,7-h]quinoline-3,9-dicarboxylic acid and sufficient lactose to make 5 grams of mixture is micropulverized and placed in an insufflator designed to deliver 50 mg. of powder per dose.

The powder is inhaled into the lungs every 4 to 6 hours for prevention of asthma attacks.

The powder is inhaled into a nostril of the nose every 4 to 6 hours for prevention of rhinitis.

EXAMPLE 11

Twelve grams of an aerosol composition are prepared from the following ingredients:

| | |
|---|---|
| Tris(hydroxymethyl)-<br>aminomethane salt of<br>1,4,7,10-tetrahydro-<br>1,7-dioxoquino[8,7-h]quino-<br>line-3,9-dicarboxylic acid | 0.025 Gm. |
| Freon 12 | 1.440 Gm. |
| Freon 114 | 2.160 Gm. |
| Water | 7.775 Gm. |
| Sorbitan monoleate | 0.600 Gm. |

The THAM salt is dissolved in the water and combined with the other constituents under pressure. The 12 grams of composition are added to a 13 cc. plastic coated bottle and capped with a metering valve. The metering valve releases 80 mg. of composition in an aerosol. The aerosol is inhaled every 4 to 6 hours for prevention of asthmatic attacks.

EXAMPLE 12

In individuals who require continual treatment in the Examples 5 through 11, the dosage of the Example is given initially and each succeeding administration of the drug is at 1/50 of the initial dosage. This maintenance dosing is continued until effective allergy prophylaxis is not obtained. The initial dosage of Examples 5 through 11 is then started once more, followed by the maintenance dosages.

EXAMPLE 13

After allowing for the differing solubilities of the compounds and the activity of the particular compound as measured by the in vivo rat passive cutaneous anaphylaxis assay, a suitable quantity of each of the compounds of Tables II and III are substituted for the active compound in the compositions and uses of Examples 5 through 11. Results showing anti-allergy activity are obtained.

EXAMPLE 14

The rat passive cutaneous anaphylaxis assay is run in the following manner:

Female Sprague-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots over the number of animals.

The tris(hydroxymethyl)aminomethane salt of 1,4,7,10-tetrahydro-1,7-dioxoquino[8,7-h]quinoline-3,9-dicarboxylic acid is prepared by dissolving the dicarboxylic acid in an equivalent weight of aqueous tris(hydroxymethyl)aminomethane and is tested in the rat passive cutaneous anaphylaxis assay in the above manner.

The inhibitory dose$_{50}$ for the tris(hydroxymethyl)-animomethane salt of 1,4,7,10-tetrahydro-1,7-dioxoquino-[8,7-h]quinoline-3,9-dicarboxylic acid, when given i.v., is 0.005 mg./kg.

I claim:
1. A pharmaceutical composition, useful for the prophylaxis of asthma or rhinitis symptoms, which comprises an anti-asthma or anti-rhinitis effective amount of a compound of the formula

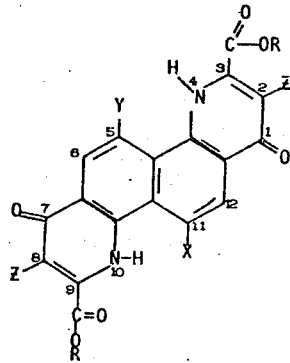

wherein
R is selected from the group consisting of hydrogen, alkyl from one to three carbon atoms, inclusive; phenyl, and a pharmaceutically acceptable metal or amine cation;
Z is selected from the group consisting of hydrogen, alkyl from one to three carbon atoms, inclusive; and phenyl;

X and Y are the same or different monosubstituents and when X and Y are different monosubstituents, one monosubstituent is hydrogen and the other monosubstituent is selected from the group consisting of alkyl from one to three carbon atoms, inclusive; alkoxy from one to three carbon atoms, inclusive; phenyl; halogen; hydroxy; nitro; trifluoromethyl; cyano; amino; carboxyamide; and

where Q is selected from the group consisting of hydrogen, alkyl from one to three carbon atoms, inclusive; phenyl, and a pharmaceutically acceptable metal or amine cation with the proviso that where R is hydrogen or a pharmaceutically acceptable metal or amine cation; then Q is the same as R; and when X and Y are the same monosubstituent, they are selected from the group consisting of hydrogen, chlorine, bromine, and methoxy in association with a pharmaceutical carrier.

2. A pharmaceutical composition in accordance with claim 1 wherein the compound is 1,4,7,10-tetrahydro-1,7-dioxoquino[8,7-h]quinoline-3,9-dicarboxylic acid.

3. A pharmaceutical composition in accordance with claim 1 wherein the compound is di-tris(hydroxymethyl)-methylammonium-1,4,7-10-tetrahydro-1,7-dioxoquino-[8,7-h]quinoline-3,9-dicarboxylate.

4. A composition in accordance with claim 1 wherein said carrier is suitable for inhalation or insufflation.

5. A process for the prophylactic treatment of asthma or rhinitis which comprises administering to a sensitized human or mammal an anti-asthma or anti-rhinitis effective amount of a compound of the formula

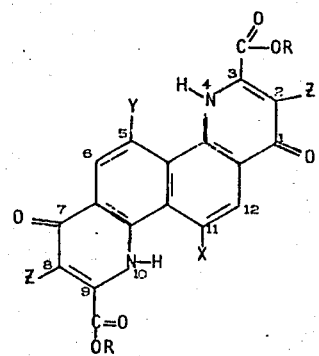

wherein
R is selected from the group consisting of hydrogen, alkyl from one to three carbon atoms, inclusive; phenyl, and a pharmaceutically acceptable metal or amine cation;
Z is selected from the group consisting of hydrogen, alkyl from one to three carbon atoms, inclusive; and phenyl;
X and Y are the same or different monosubstituents and when X and Y are different monosubstituents, one monosubstituent is hydrogen and the other monosubstituent is selected from the group consisting of alkyl from one to three carbon atoms, inclusive; alkoxy from one to three carbon atoms, inclusive; phenyl; halogen; hydroxy; nitro; trifluoromethyl; cyano; amino; carboxyamide; and

where Q is selected from the group consisting of hydrogen, alkyl from one to three carbon atoms, inclusive; phenyl, and a pharmaceutically acceptable metal or amine cation with the proviso that where R is hydrogen or a pharmaceutically acceptable metal or amine cation, then Q is the same as R; and when X and Y are the same monosubstituent, they are selected from the group consisting of hydrogen, chlorine, bromine, and methoxy in association with a pharmaceutical carrier.

6. A process in accordance with claim 5 wherein the compound is 1,4,7,10-tetrahydro-1,7-dioxoquino-[8,7-h]quinoline-3,9-dicarboxylic acid.

7. A process in accordance with claim 5 wherein the compound is di-tris(hydroxymethyl)methylammonium-1,4,7,-10-tetrahydro-1,7-dioxoquino[8,7-h]quinoline-3,9-dicarboxylate.

8. A process in accordance with claim 5 wherein the compound is administered by insufflation or inhalation.

9. A process in accordance with claim 5 wherein the compound is administered orally.

* * * * *